US012779220B2

(12) United States Patent
Ahn

(10) Patent No.: US 12,779,220 B2
(45) Date of Patent: Nov. 3, 2026

(54) ELECTRIC DEVICE FOR SKIN TREATMENT AND CONTROL METHOD THEREFOR

(71) Applicant: AGNES MEDICAL CO., LTD., Seongnam-si (KR)

(72) Inventor: Gunyoung Ahn, Seongnam-si (KR)

(73) Assignee: AGNES MEDICAL CO., LTD., Seongnam-si (KR)

( * ) Notice: Subject to any disclaimer, the term of this patent is extended or adjusted under 35 U.S.C. 154(b) by 1183 days.

(21) Appl. No.: 17/836,465

(22) Filed: Jun. 9, 2022

(65) Prior Publication Data

US 2022/0409898 A1 Dec. 29, 2022

(30) Foreign Application Priority Data

Jun. 23, 2021 (KR) ........................ 10-2021-0081694

(51) Int. Cl.
*A61N 1/36* (2006.01)
*A61N 1/05* (2006.01)

(52) U.S. Cl.
CPC ....... *A61N 1/36034* (2017.08); *A61N 1/0502* (2013.01); *A61N 1/36017* (2013.01); *A61N 1/36031* (2017.08)

(58) Field of Classification Search
CPC .............. A61N 1/36034; A61N 1/0502; A61N 1/36017; A61N 1/36031; A61N 1/36021; A61N 1/328; A61N 1/06; A61N 1/08; A61M 5/3298; A61M 2205/054
See application file for complete search history.

(56) References Cited

U.S. PATENT DOCUMENTS 8,666,487 B2 * 3/2014 Kang ..................... A61B 18/14
604/173
10,561,800 B2 * 2/2020 Marlin ................ A61M 5/3234

FOREIGN PATENT DOCUMENTS

KR 101122526 B1 * 3/2012 ............... A61N 1/08
KR 20160111191 A * 9/2016 ........... A61N 1/0412
KR 10-1664245 B1 10/2016
KR 10-2018-0101763 A 9/2018
KR 10-2020-0025846 A 3/2020
(Continued)

OTHER PUBLICATIONS

KR 101122526 B1—Translation (Year: 2012).*
(Continued)

*Primary Examiner* — Niketa Patel
*Assistant Examiner* — Attiya Sayyada Hussaini
(74) *Attorney, Agent, or Firm* — Paratus Law Group, PLLC

(57) ABSTRACT

An electric device for skin treatment, includes: a needle body including needles for drug injection and electrical stimulation treatment and a needle printed circuit board (PCB) connected to the needles; a needle cap provided at a first end of the needle body and having a needle hole through which the needles passes; and a handpiece body having a first end detachably connected to a second end of the needle body. The handpiece body includes: a connection PCB to which a connection member configured to be electrically connected to the needle PCB is coupled; and a connection PCB cable configured to be electrically connected to the connection PCB.

6 Claims, 7 Drawing Sheets

(56) References Cited

FOREIGN PATENT DOCUMENTS

| | | | | | | |
|---|---|---|---|---|---|---|
| KR | 10-2021-0045239 | A | | 4/2021 | | |
| KR | 20210045239 | A | * | 4/2021 | .......... | A61M 5/3298 |

OTHER PUBLICATIONS

KR20160111191_Translation (Year: 2016).*
KR20210045239A Translation (Year: 2021).*
Korean Office Action for related KR Application No. 10-2021-0081694 mailed Dec. 20, 2022 from Korean Intellectual Property Office.

* cited by examiner

ELECTRIC DEVICE FOR SKIN TREATMENT AND CONTROL METHOD THEREFOR

CROSS-REFERENCE TO PRIOR APPLICATION

This application claims priority to Korean Patent Application No. 10-2021-0081694 (filed on Jun. 23, 2021), which is hereby incorporated by reference in its entirety.

BACKGROUND

The present disclosure relates to an electric device for skin treatment and a control method therefor, and more particularly, to an electric device for skin treatment for protecting a user from a risk of electric shock and a control method therefor.

A high-frequency current used for skin treatment generally refers to an alternating current of 100,000 Hz or more. Since the high-frequency current has a very short vibration width, it hardly causes ion movement when passing through human tissues and does not cause electrochemical reactions or electrolysis. In addition, when high-frequency electrical energy is applied to the tissues, molecules constituting each tissue vibrate and rub against each other whenever the direction of the electric current is changed, thereby generating bio-heat.

Unlike other current types, such a high-frequency current does not stimulate sensory and motor nerves and do not cause discomfort or muscle contraction in the human body. In addition, the high-frequency current has the advantage of generating thermal energy as mentioned above, and this thermal energy enhances functions of cells and increasing a blood flow volume.

Accordingly, a skin treatment device using high frequencies is used for various treatment purposes such as skin regeneration, skin lifting, suppression of melanin secretion, obesity treatment, skin care, hair growth stimulation, and pain relief.

Specifically, when it comes to skin treatment, an electrical directly transfers energy such as a high-frequency current to the dermal layer of the skin through needles to activate cell tissues, thereby toning the skin and minimizing the aging of the skin.

However, in an existing electrical treatment device, a contact terminal connected to needles protrudes to the outside of a handpiece in order to allow a current to flow through the needles. Thus, a user is put at a risk of electric shock and since used needles must be periodically replaced, the contact terminal may be damaged in a process of the replacement of the needles.

SUMMARY

The present disclosure provides an electric device for skin treatment having a structure capable of solving the above-described problems and a method for controlling the same.

First, the present disclosure provides an electric device for skin treatment and a control method therefor, the electric device in which a contact terminal in contact with needles is in contact with the needles without protruding externally.

In addition, the present disclosure also provides an electric device for skin treatment and a control method therefor, the electric device in which a connection member connected to needles does not protrude externally when the needles are not assembled, thereby preventing a risk of electric shock.

The technical objects of the present disclosure are not limited to the aforementioned technical objects, and other technical objects, which are not mentioned above, will be apparent to those skilled in the art from the following description.

In an aspect, there is provided an electric device for skin treatment, the device including: a needle body including needles for drug injection and electrical stimulation treatment and a needle printed circuit board (PCB) connected to the needles; a needle cap provided at a first end of the needle body and having a needle hole through which the needles passes; and a handpiece body having a first end detachably connected to a second end of the needle body, wherein the handpiece body comprises: a connection PCB to which a connection member configured to be electrically connected to the needle PCB is coupled; and a connection PCB cable configured to be electrically connected to the connection PCB.

The needle body may comprise a plated part disposed at the second end of the needle body and providing the needle with a current in contact with the connection member.

The handpiece body may comprise a connection member cover disposed at one end of the handpiece body and including a through hole through which the connection member is passed, and when the needle body is connected to the handpiece body, a first end of the connection member may protrude externally from the handpiece body through the through hole and then is electrically connected to the plated part.

The handpiece body may further comprises a sensor configured to detect a contact between the user and the handpiece body.

The connection member may comprise a first connection member providing the needles with a current in contact with the plated part.

The connection member may comprise a second connection member electrically connected to the sensor part to detect whether the connection member is in contact with the plated part.

The needle body may comprise a protrusion disposed at the other end of the needle body and insertable into the handpiece body, and the handpiece body may comprise an insertion hole into which the protrusion to be inserted.

The needles may have different heights from each other.

In another aspect, there is provided a control method for an electric device for skin treatment, the method including: setting a position of a motor inside a handpiece body based on control information generated by a controller when a driving power is applied; checking a set position of the motor and operating a foot switch; applying a current to the needles when a user is detected by the sensor part of the handpiece body and the foot switch is in operating; and returning back to the checking when the user is not detected by the sensor part of the handpiece body and the foot switch is in operating.

The applying comprises detecting whether a connection member is in contact with a plated part of a needle body, and the returning comprises blocking the current applied to the needles when the connection member is not in contact with the plated part of the needle body.

According to the electric device for skin treatment according to an embodiment of the present disclosure, a current may be applied to needles through a connection PCB cable disposed inside the handpiece body. Due to this, the frequency of breakdown is lower than when the connection PCB cable is exposed to the outside, and the risk of electric shock is also eliminated for the user and the therapist. Accordingly, user convenience may be increased.

In addition, according to the electric device for skin treatment according to an embodiment of the present disclosure, in the connection member cover provided with a through hole, the connection member is electrically connected to the plate part of the needle part only the needle body part and the handpiece body part are coupled, and when the needle body and the handpiece body are not coupled, one side of the connection member does not protrude externally from the handpiece body, thereby preventing a risk of electric shock to the user and the person in therapy.

Effects of the present disclosure are not limited to the effects mentioned above, and other effects not mentioned will be clearly understood by those skilled in the art from the following description.

DETAILED DESCRIPTION

Advantages and features of the present disclosure and a method of achieving the same should become clear with embodiments described in detail below with reference to the accompanying drawings. However, the present disclosure is not limited to the embodiments disclosed below and may be realized in various other forms. The present embodiments make the disclosure complete and are provided to completely inform one of ordinary skill in the art to which the present disclosure pertains of the scope of the disclosure. The present disclosure is defined only by the scope of the claims.

Terms used herein are for describing the embodiments and are not intended to limit the present disclosure. In the present specification, a singular expression includes a plural expression unless the context clearly indicates otherwise. "Comprises" and/or "comprising" used herein do not preclude the existence or the possibility of adding one or more elements other than those mentioned. Terms such as "comprises" and/or "comprising" used in the specification do not exclude the existence or addition of one or more other components. Terms such as "first" and "second" may be used to describe various components, but it is apparent that the various components are not limited by the terms. Those terms are only used for the purpose of differentiating a component from other components. Therefore, it is apparent that a first component which will be described below may be referred to as a second component without departing from the technical spirit of the present disclosure.

The term "horizontal direction" used in the following description refers to a forward, rearward, leftward, or rightward direction in a state where the position of an upward or downward direction does not change, and the term "vertical direction" used in the following description means an upward or downward direction in a state in which the position of a forward, rearward, leftward, or rightward direction does not change.

Unless otherwise defined, all terms including technical and scientific terms used herein have the same meaning as commonly understood by one of ordinary skill in the art to which the present disclosure pertains. In addition, terms, such as those defined in commonly used dictionaries, are not to be construed in an idealized or overly formal sense unless expressly so defined herein.

Hereinafter, an embodiment of the present disclosure will be described in detail with reference to the accompanying drawings.

Figure 1:
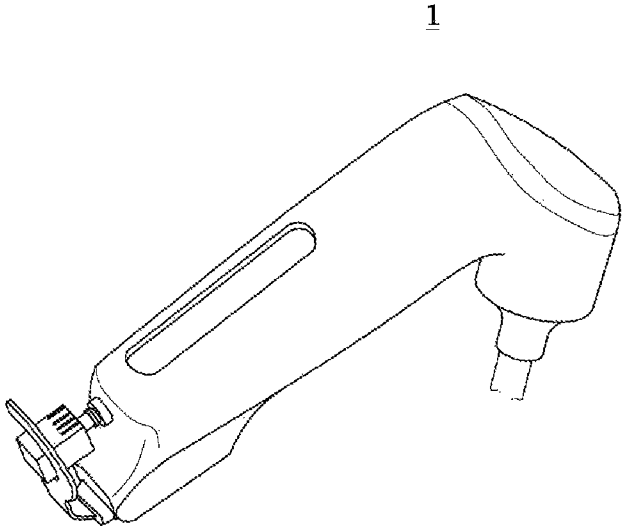
FIG. 1 is a perspective view showing the exterior appearance of a conventional skin treatment device.

1. Configurations of an Electric Device 10 for Skin Treatment According to an Embodiment of the Present Disclosure and a Combination Thereof FIG. 1 is a perspective view showing the exterior appearance of a conventional skin treatment device 1, and FIG. 2 is a configuration view showing an electric device 10 for skin treatment according to the present disclosure.

Figure 2:
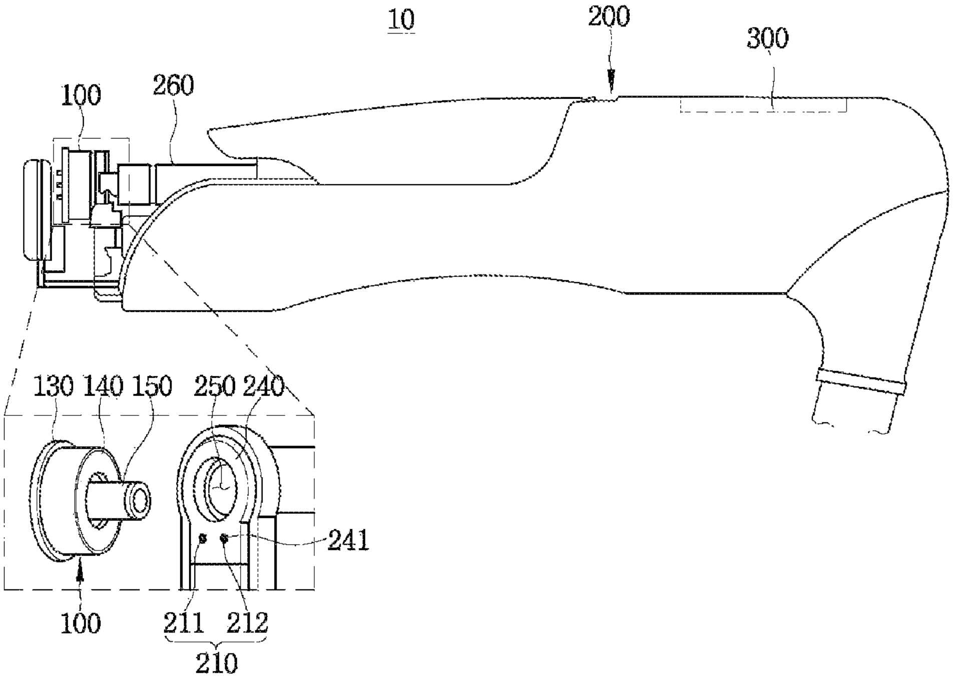
FIG. 2 is a block diagram showing an electric device for skin treatment according to the present disclosure.

Referring to FIG. 2, the electric device 10 for skin treatment according to the illustrated embodiment may include a needle body 100 and a handpiece body 200.

The needle body 100 may include a needle cap 130, a plated part 140, and a protrusion part 150 so that drug injection or electrical stimulation treatment can be performed on the skin.

The needle body 100 may be configured to be detachably attached to the handpiece body 200 through the protrusion 150 of the needle body 100. Specifically, the protrusion 150 of the needle body 100 may be inserted and coupled to an insertion hole 250 of the handpiece body 200.

A detailed description of the needle body 100 will be provided later.

The handpiece body 200 may be provided in a streamlined shape, which makes a user to conveniently perform skin treatment while holding the electronic device 10 in his/her hands. In addition, handpiece body 200 may include a connection member 210 and a connection member cover 240, a sensor part 300, and the like.

The connection member 210 may include a first connection member 211 and a second connection member 212, and the connection member 210 may be disposed in through holes 241 provided in the connection member cover 240.

The first connection member 211 may be configured to transfer a current to the needle 110 while in contact with the plated part 140.

The second connection member 212 may be configured to detect a contact between the second connection member 212 and the plated part 140 in order to determine whether the needle body 100 and the handpiece body 200 are coupled, and the second connection member may be electrically connected to the sensor part 300 which will be described later.

The sensor part 300 may be disposed at an outer surface of the handpiece body 200 and detect a contact between the user and the handpiece body 200. Specifically, the sensor part 300 may detect whether the user holds the electric device 10 for skin treatment in his/her hand.

Figure 3:
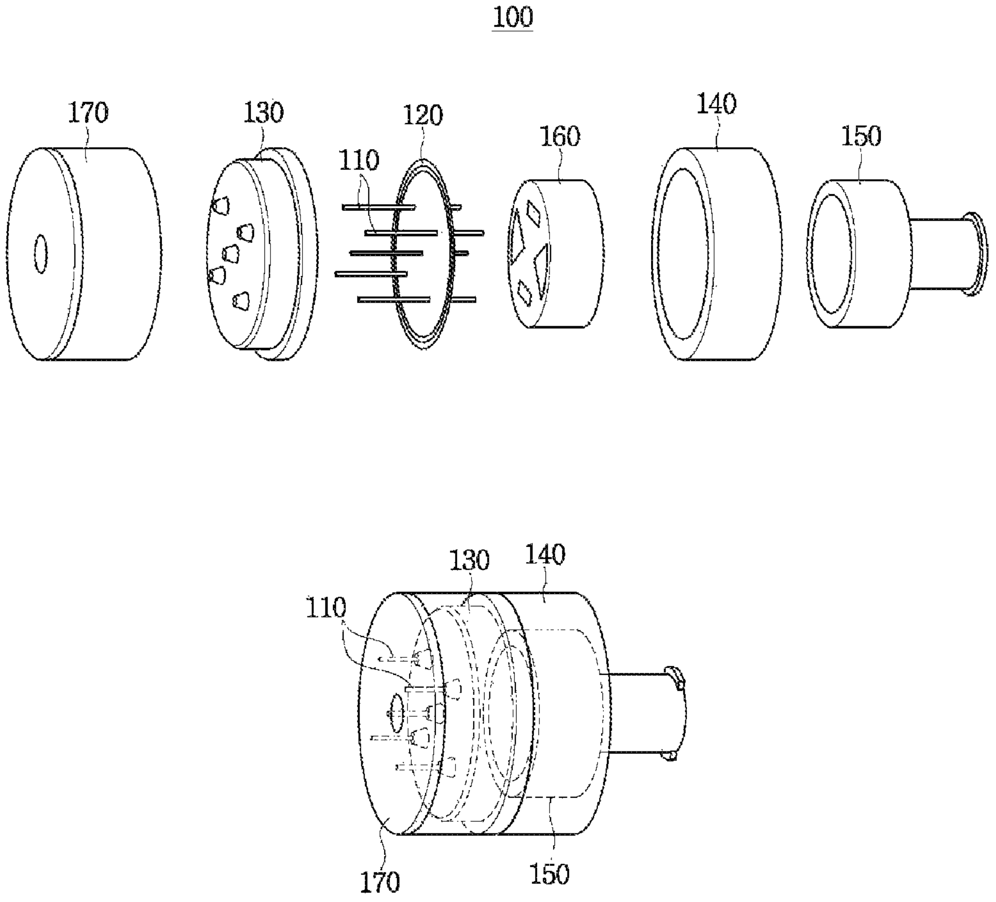
FIG. 3 is an exploded view showing the configuration of the needle body of FIG. 2.

FIG. 3 is an exploded view showing the configuration of the needle body 100 of FIG. 2.

Referring to FIG. 3, the needle body 100 may include a needle 110, a needle printed circuit board (PCB) 120, the needle cap 130, the plated part 140, the protrusion 150, a drug receiving part 160, and a needle housing cap 170.

The needle 110 may be easily mounted to the needle body 100 and configured to improve user convenience. Specifically, a longitudinal direction of the needle 110 may be vertically connected to a cross section of the needle PCB 120 which will be described later.

The needle 110 may be formed of an electrically conductive material and may be provided in plural. In addition, the needles 110 may be individually mounted to the needle body 100, facilitating sterilization and cleaning.

When a plurality of needles 110 is provided, the respective needles 110 may be arranged at the same height. However, the needles 110 are not limited to having the same height and may be configured to have different heights based on the user's selection.

In addition, although not shown, a needle 110 for the purpose of drug treatment and a needle 110 for the purpose of electrical stimulation may be provided separately, and a plurality of separate needles 110 for the respective purposes thereof may be connected to the needle PCB 120 described above.

In addition, although not shown, an electrical connection terminal (not shown) may be disposed at one end of a needle 110 and coupled to the needle PCB 120 which will be described later. Accordingly, a current may flow in the needle 110.

The needle PCB 120 may be a printed circuit board that applies a current to the needle 110 using power supplied from a power supply device (not shown). In this case, the needle PCB 120 may be preferably configured as a flexible printed circuit board (FPCB) to have flexibility.

The needle PCB 120 may have one or more contact holes (not shown) disposed therein, and the needle 110 may pass through the contact holes (not shown). Alternatively, the needle 110 and the needle PCB 120 may be electrically connected to each other as the electrical connection terminal (not shown) of the needle 110 is coupled to the needle PCB 120.

The needle cap 130 may serve to hold the needle 110 in place without shaking so that the needle 110 can be stably maintained without any damage while the needle 110 is inserted into the skin of a person in therapy.

The needle cap 130 may be provided at one end of the needle body 100, and the needle 110 may pass through a needle hole 131 formed in the needle cap 130.

The plated part 140 may be disposed at the other end of the needle body 100. One end of the plated part 140 may contact the needle PCB 120 and the other end of the plated part 140 may contact the connection member 210, so that a current can be transferred to the needle 110. To this end, the plated part 140 may be preferably formed of an electrically conductive material.

The protrusion 150 may be formed at the other end of the needle body 100 to extend in the longitudinal direction and may be insertable into the handpiece body 200 as described above.

The drug receiving part 160 may have a space in which drug is accommodated so that drug introduced from the drug delivery part 260, which will be described later, can be delivered to the needle 110. The drug receiving part 160 may be connected to the other end of the needle 110 passing through the needle PCB 120.

The drug receiving part 160 may be inserted into an inner space formed on one side of the protrusion 150, with an outer surface of the drug receiving part 160 corresponding to an inner surface of the protrusion 150.

The needle housing cap 170 may be disposed at one end of the needle body 100 and may be coupled to the needle cap 130 so that the needle 110 can be disposed in the needle housing cap 170.

The needle housing cap 170 may serve to protect the user or the person in therapy from the needle 110.

Figure 4:
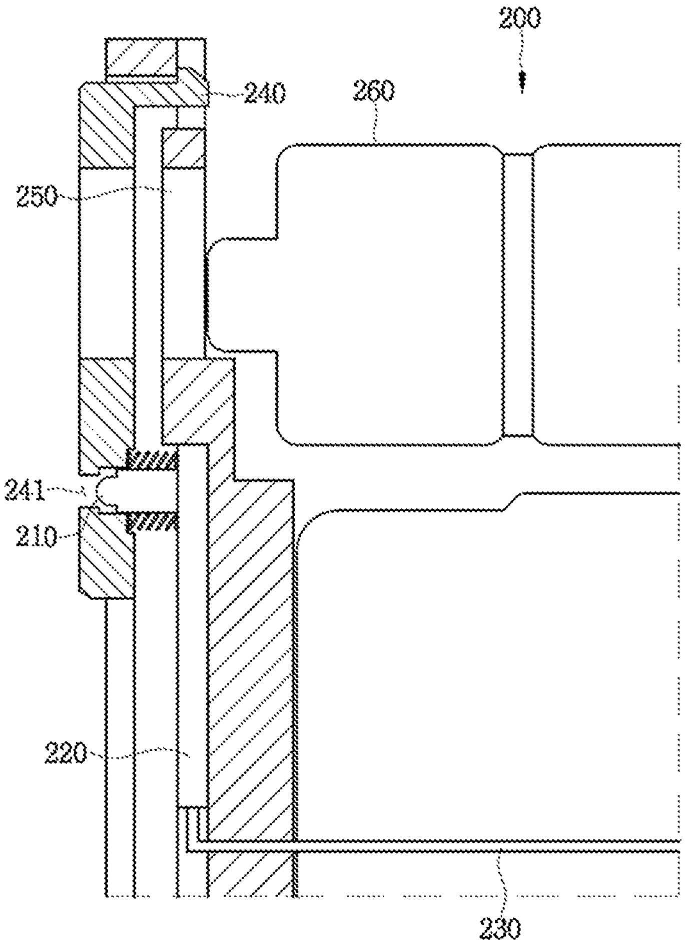
FIG. 4 is a cross-sectional view showing a portion of the handpiece body of FIG. 2.

FIG. 4 is a cross-sectional view showing a portion of the handpiece body 200 of FIG. 2.

Referring to FIG. 4, the handpiece body 200 may be provided in a streamlined shape in which a user can easily perform treatment on the skin of a person in therapy while holding the electric device 10 in his/her hand.

As described above, the handpiece body 200 may be provided with an insertion hole 250 formed in one side of the handpiece body 200, so that one end of the handpiece body 200 is detachably attached to the other end of the needle body 100. In this case, a through hole through which the other end of the needle body 100 is detachable may be provided in the connection member cover 240 to correspond to the position of the insertion hole. Specifically, the aforementioned protrusion 150 may be inserted and coupled to the handpiece body 200 through the insertion hole 250 and the through hole.

The handpiece body 200 may also include the connection member 210, the connection PCB 220, a connection PCB cable 230, the connection member cover 240 and a drug delivery part 260.

The connection member 210 of the present disclosure may be electrically connected to the other end of the plated part 140 and the aforementioned connection PCB 220.

Specifically, in this case, it may be preferable that one end of the connection member 210 is in close contact with the other end of the plated part 140 and the other end of the connection member 210 is in close contact with the connection PCB 220.

The connection member 210 may be formed of a conductive material so that there is no problem in a current flowing through the plating unit 140, the connection member 210, and the connection PCB 220 through both ends of the connection member 210. For example, the connection member 210 may be formed of metal such as copper, silver, or aluminum. In addition, the connection member 210 may include an elastic member (not shown) or may be formed in a shape deformable by elasticity to allow a current to flow through the both ends of the connection member 210. For example, the connection member 210 may be formed as a pogo pin, a leaf spring, a terminal connector, a pin connector, and the like.

Meanwhile, as described above, the connection member cover 240 may be disposed at one end of the handpiece body 200 and include the through hole 241, and one side of the connection member 210 may be positioned inside the through hole 241. In this case, in a case where the needle body 100 is not coupled to the handpiece body 200, the connection member cover 240 does not apply a force in the longitudinal direction of the connection member 210, and thus, the one side of the connection member 210 does not protrude externally from the through hole 241.

The connection PCB 220 may be coupled to the connection member 210 so that the connection PCB 220 can be electrically connected to the needle PCB 120.

Unlike an existing technology in which a connection PCB cable protrudes externally, the connection PCB cable 230 may be disposed inside the handpiece body 200 and may be configured to be electrically connected to the connection PCB 220.

In a case where the connection PCB cable 230 is disposed inside the handpiece body 200, a failure less likely occurs and the risk of electric shock to a user and a person in therapy may be lowered.

The connection member cover 240 may be configured to prevent one side of the connection member 210 of the handpiece body 200 from protruding externally by electricity of the elastic member (not shown) provided in the connection member 210 in a case where the needle body 100 is not coupled to the handpiece body 200.

Also, the risk of electric shock to the user and the therapist can be prevented.

The drug delivery part 260 is configured to deliver drug injected into the skin to the aforementioned drug receiving part 160, and is disposed inside the handpiece body 200.

Figure 5A:
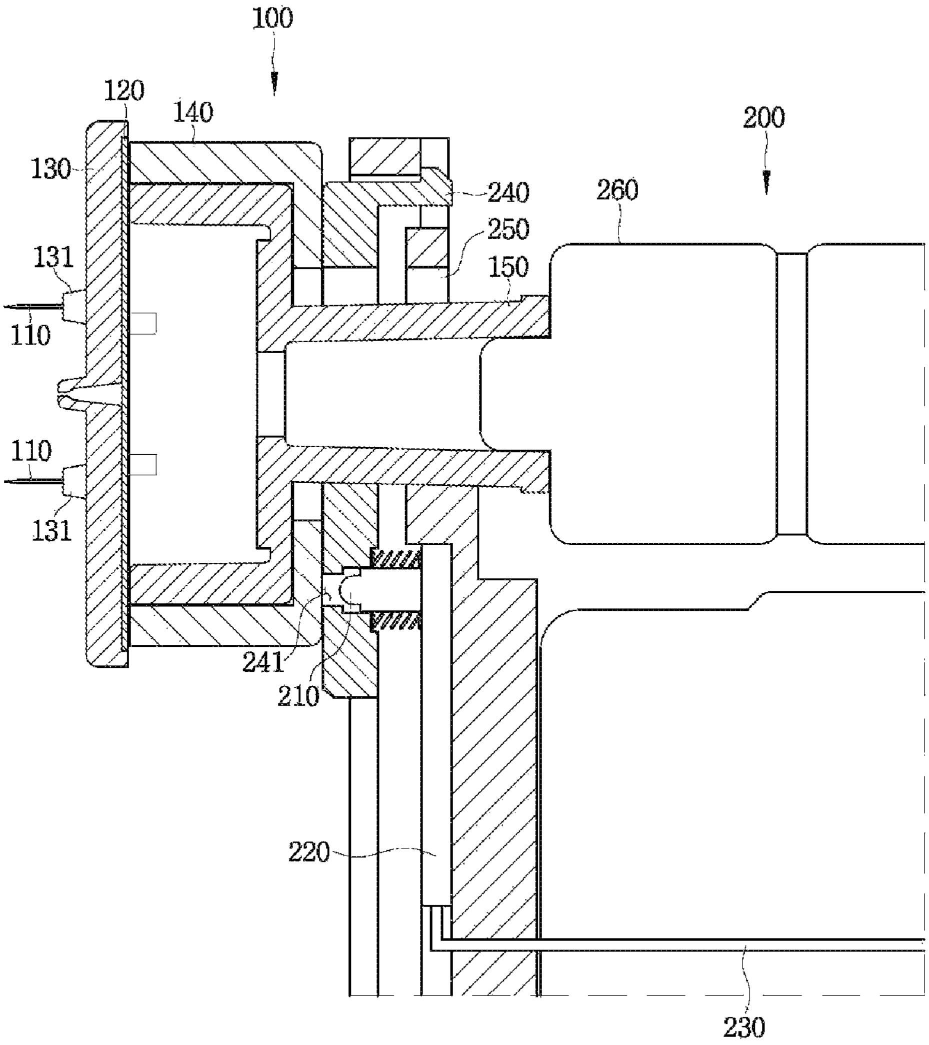
FIG. 5A is a conceptual view showing the coupling of the needle body and the handpiece body of FIG. 2.
Figure 5B:
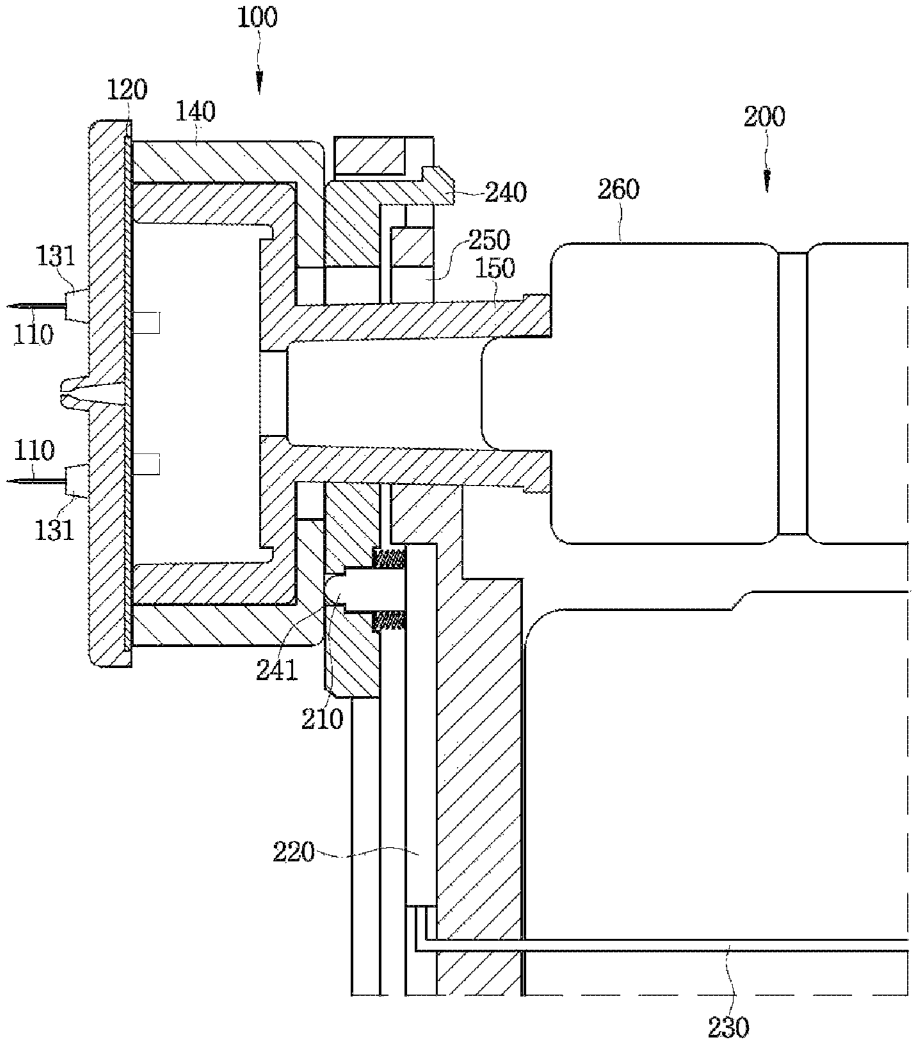
FIG. 5B is a conceptual view showing the operation of FIG. 5A.

FIG. 5A is a conceptual view showing the coupling of the needle body 100 and the handpiece body 200 shown in FIG. 2, and FIG. 5*b* is a conceptual view showing the operation of FIG. 5A.

Referring to FIGS. 5A and 5B, the plated part 140 may be disposed at the other end of the needle body 100 and one side of the plated part 140 may be connected to the needle PCB 120. When the other side of the plated part 140 is in contact with the connection member 210, a current may be supplied to the needle 110.

To this end, in the case of coupling the needle body 100 and the handpiece body 200 to each other, the plated part 140 of the needle body 100 may come in close contact with the connection member cover 240 and the elastic member (not shown) inside the connection member 210 may be compressed, thereby allowing the protrusion 150 to be inserted into the insertion hole 250 until one side of the connection member 210 comes into contact with the plated part 140 through the through hole 241.

Referring back to FIG. 2, in this case, the first connection member 211 may be in contact with the plated part 140 and electrically connected thereto and may transfer a current to the needle 110.

One end of the drug delivery part 260 may be connected to the other end of the protrusion 150 when the needle body 100 is coupled to the handpiece body 200, and the inside of the protrusion 150 should be penetratingly formed in the longitudinal direction so that drug in the drug delivery unit 260 can move to the drug receiving part 160.

Figure 6:
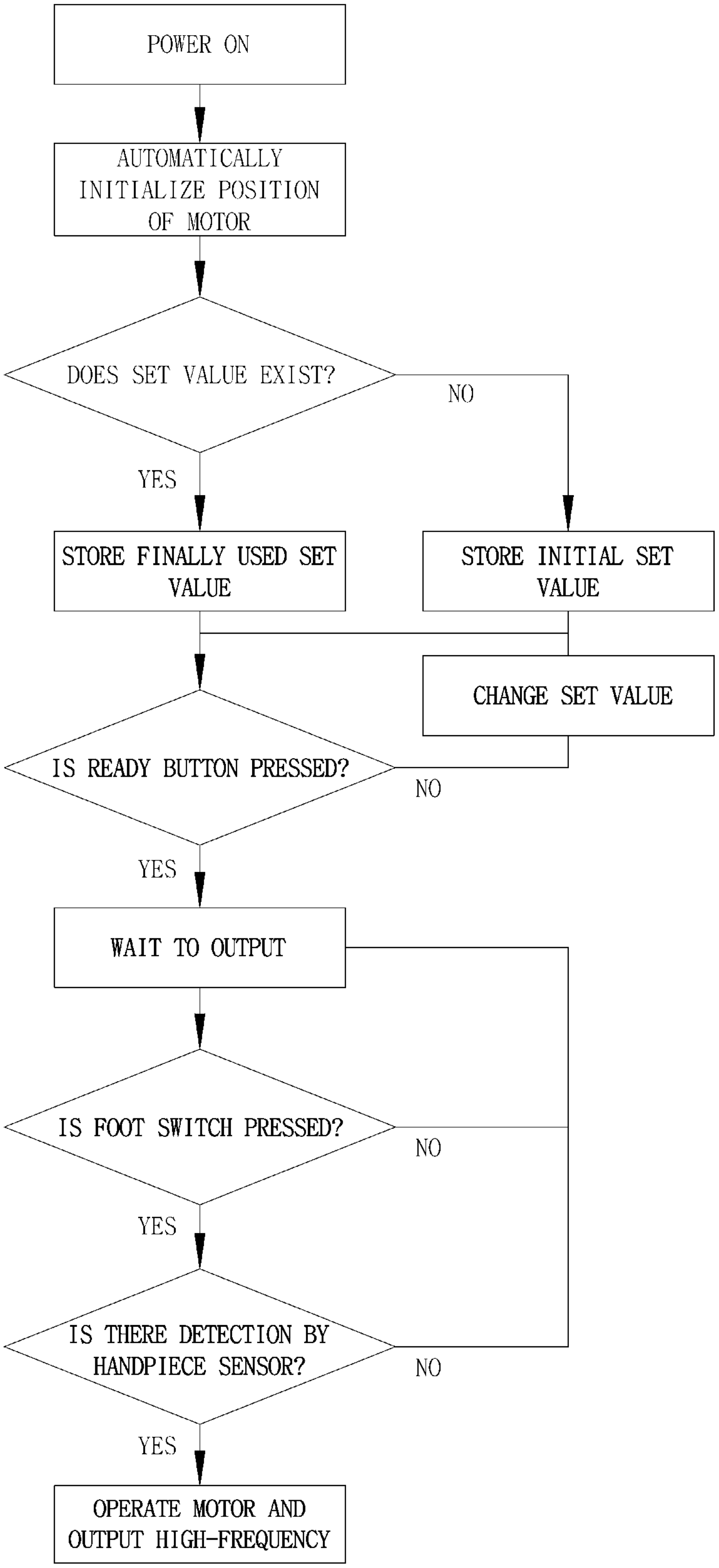
FIG. 6 is a flowchart illustrating a control method for an electric device for skin treatment according to an embodiment of the present disclosure.
Figure 7:
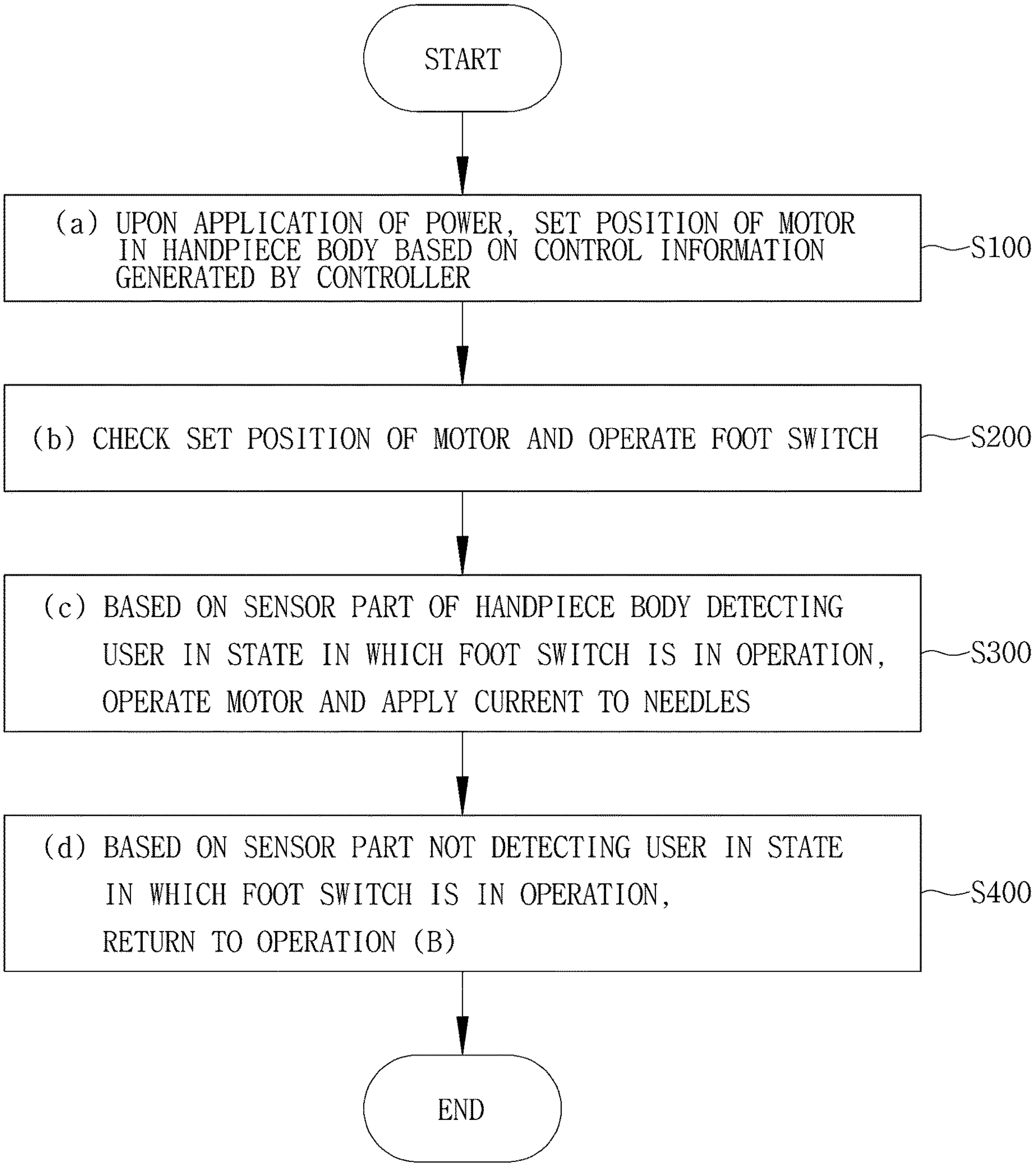
FIG. 7 is another flowchart illustrating a control method for an electric device for skin treatment according to an embodiment of the present disclosure.

2. Control Method for the Electric Device 10 for Skin Treatment According to an Embodiment of the Present Disclosure FIG. 6 is a flowchart illustrating a control method for the electric device 10 for skin treatment according to an embodiment of the present disclosure, and FIG. 7 is another flow chart illustrating a control method of the electric device 10 for skin treatment according to an embodiment of the present disclosure.

The present disclosure will be described with reference to FIGS. 6 and 7 as follows.

First, upon application of power, a position of a motor (not shown) in a handpiece body 200 may be set in operation S100 based on control information generated by a controller. In this case, the set position of the motor (not shown) may refer to an initial position of the motor defined by a user.

Thereafter, the user may check the set position of the motor (not shown) and operate a foot switch in operation S200. In this case, the foot switch is a commonly known technology and serves to supply power to the handpiece body 200 from a power supply device (not shown). Power may be connected when the user presses the foot switch to operate, and the power may be cut off when the user takes his/her foot off the foot switch to stop the operation.

In this case, when the foot switch is in operation and the sensor part 300 of the handpiece body 200 detects a user at the same time, the motor (not shown) is operated and a current is applied to the needle 110 in operation S300.

In this case, the sensor part 300 may detect whether the second connection member 212 is in contact with the plated part 140 of the needle body 100. Information that the sensor part 300 detects the user is transmitted to the controller (not shown). The controller (not shown) may supply power to the connection PCB cable 230 when the sensor part 300 detects the contact of the user.

On the other hand, when the sensor part 300 of the handpiece main body 200 may not detect the user although the foot switch is in operation, the motor (not shown) is not operated and a high-frequency current is not applied to the needle 110 in operation S400.

Specifically, when the second connection member 212 is in non-contact with the plated part 140 of the needle body 100 and the sensor part 300 detects the non-contact and transmits information on the non-contact to the controller (not shown), the controller (not shown) may not supply power to the connection PCB cable 230.

In addition, even when the foot switch is not operated although the sensor part 300 of the handpiece body 200 detects the user, the motor (not shown) may not be operated and a high-frequency current may not be applied to the needle 110.

Although embodiments of the present disclosure have been described with reference to the accompanying drawings, it will be apparent to those skilled in the art that various modifications and variation can be made in the present disclosure without departing from the spirit or scope of the invention. Therefore, it should be understood that the embodiments described above are illustrative in all respects and not restrictive.

What is claimed is:

1. An electric device for skin treatment, the device comprising:
- a needle body including needles for drug injection and electrical stimulation treatment and a needle printed circuit board (PCB) connected to the needles;
- a needle cap provided at a first end of the needle body and having a needle hole through which the needles passes; and
- a handpiece body having a first end detachably connected to a second end of the needle body,
- wherein the handpiece body comprises:
  - a connection PCB to which a connection member configured to be electrically connected to the needle PCB is coupled; and
  - a connection PCB cable configured to be electrically connected to the connection PCB,
- wherein the needle body comprises a plated part disposed at the second end of the needle body and providing the needle with a current in contact with the connection member,
- wherein:
- the handpiece body comprises a connection member cover disposed at one end of the handpiece body and including a through hole through which the connection member is passed, and
- when the needle body is connected to the handpiece body, a first end of the connection member protrudes externally from the handpiece body through the through hole and then is electrically connected to the plated part.

2. The electric device of claim 1, wherein the handpiece body further comprises a sensor configured to detect a contact between the user and the handpiece body.

3. The electric device of claim 2, wherein the connection member comprises a second connection member electrically connected to the sensor to detect whether the connection member is in contact with the plated part.

4. The electric device of claim 1, wherein the connection member comprises a first connection member providing the needles with a current in contact with the plated part.

5. The electric device of claim 1, wherein:

the needle body comprises a protrusion disposed at the second end of the needle body and insertable into the handpiece body, and the handpiece body comprises an insertion hole into which the protrusion to be inserted.

6. The electric device of claim 1, wherein the needles have different heights from each other.

* * * * *